United States Patent
Ogura et al.

(10) Patent No.: US 6,811,532 B2
(45) Date of Patent: Nov. 2, 2004

(54) ENDOSCOPE

(75) Inventors: Takeshi Ogura, Fussa (JP); Masanori Hamazaki, Hachioji (JP); Haruhiko Kaiya, Hachioji (JP); Toshio Nakamura, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/968,943

(22) Filed: Oct. 2, 2001

(65) Prior Publication Data

US 2002/0099266 A1 Jul. 25, 2002

(30) Foreign Application Priority Data

Oct. 2, 2000 (JP) ........................................ 2000-302470
Jul. 31, 2001 (JP) ........................................ 2001-232166

(51) Int. Cl.$^7$ ................................................. A61B 1/00
(52) U.S. Cl. ........................................ 600/146; 600/139
(58) Field of Search ................................. 600/114, 131, 600/139, 141, 146, 147, 148, 149, 150, 434, 435, 585; 604/45.01, 95.04

(56) References Cited

U.S. PATENT DOCUMENTS

| | | | | |
|---|---|---|---|---|
| 3,557,780 A | * | 1/1971 | Sato | 600/141 |
| 3,799,151 A | * | 3/1974 | Fukaumi et al. | 600/142 |
| 4,932,394 A | * | 6/1990 | Nanaumi | 600/148 |
| 5,025,804 A | * | 6/1991 | Kondo | 600/146 |
| 5,179,935 A | * | 1/1993 | Miyagi | 600/142 |
| 5,464,007 A | * | 11/1995 | Krauter et al. | 600/144 |
| 5,482,029 A | * | 1/1996 | Sekiguchi et al. | 600/109 |
| 5,512,035 A | * | 4/1996 | Konstorum et al. | 600/146 |
| 5,787,897 A | * | 8/1998 | Kieturakis | 128/898 |
| 5,916,147 A | * | 6/1999 | Boury | 600/146 |
| 6,033,378 A | * | 3/2000 | Lundquist et al. | 604/95.01 |
| 6,066,090 A | * | 5/2000 | Yoon | 600/113 |
| 6,402,686 B1 | * | 6/2002 | Ouchi | 600/139 |
| 6,413,234 B1 | * | 7/2002 | Thompson et al. | 604/95.04 |
| 6,482,149 B1 | * | 11/2002 | Torii | 600/142 |

FOREIGN PATENT DOCUMENTS

JP    Hei 5-16857    3/1993

* cited by examiner

*Primary Examiner*—Beverly M. Flanagan
(74) *Attorney, Agent, or Firm*—Scully, Scott, Murphy & Presser

(57) ABSTRACT

An endoscope has a first bending portion and a second bending portion. The first bending portion is the distal portion of an elongated insertion member, and the second bending portion is located at the proximal end of the first bending portion. The dimension of the second bending portion in the longitudinal axis of the insertion member is smaller than the dimension of the first bending portion therein. The endoscope includes a hand-held unit having a control section that is used to bend the first bending portion and second bending portion. The control section of the hand-held unit has an angling knob that is used to bend the first bending portion, and a second angling lever that is used to bend the second bending portion.

38 Claims, 19 Drawing Sheets

ENDOSCOPE

This application is based upon and claims the benefit of priority from the prior Japanese Patent Application No. 2000-302470, filed on Oct. 2, 2000 and No. 2001-232166 filed on Jul. 31, 2001 in Japan, the entire contents of which are incorporated herein by reference.

BACKGROUND OF THE INVENTION

1. Field of the Invention

The present invention relates to an endoscope, or more particularly, to an endoscope having two bending portions of a first bending portion and a second bending portion.

2. Description of the Related Art

Endoscopes have an elongated insertion member thereof inserted into a three-dimensionally complexly tortuous and narrow lumen of the stomach, the intestine, or any other organ of a living tissue, or a three-dimensionally complexly tortuous and narrow hollow of a machine in conformity with the shape of the lumen or hollow. The insertion member must therefore be angled three-dimensionally finely.

For example, an endoscope described in Japanese Examined Patent Application Publication No. 5-16857 has two bending portions of a first bending portion and a second bending portion. The first bending portion is the distal portion of an elongated insertion member and has a plurality of joint pieces concatenated so that the joint pieces can rotate freely. The second bending portion is located at the proximal end of the first bending portion. A hand-held unit having a control section that is used to bend the first bending portion and second bending portion has an angling mechanism. The sole angling mechanism enables selective bending of the first bending portion and second bending portion.

However, when the insertion member of an endoscope has two bending portions, the lengths of the bending portions have a significant meaning.

For example, assume that a narrow lumen such as the lumen of the large intestine is observed. In this case, if the second bending portion that is the proximal portion is longer, when the second bending portion is bent, the bending portion including the first and second bending portions is entirely largely moved. It is therefore hard to finely adjust the position of the distal part of the endoscope. This eventually poses a problem that observation is hard to achieve.

For example, when the cardia of the stomach and its surroundings are observed by viewing the face of the cardia, the first bending portion is largely bent in an Up direction and the second bending portion is bend in a Down direction. The distal part of an endoscope may thus be made to approach the cardia. When the second bending portion is long, although the second bending portion has not fully come out of the esophagus, the whole bending portion including the first and second bending portions must be bent. It is therefore hard to bend the second bending portion. This results in unsuccessful observation.

The present invention attempts to break through the foregoing situation. The present invention aims to provide an endoscope capable of offering improved ease of observation with a second bending portion thereof bent and with a distal portion of an insertion member thereof faced a desired position.

SUMMARY OF THE INVENTION

Accordingly, an object of the present invention is to provide an endoscope offering improved ease of observation with a distal portion of an insertion member thereof faced a desired position.

Another object of the present invention is to provide an endoscope having two bending portions that can be bent independently of each other, and offering ease of bending of the same level as that an endoscope having one bending portion offers.

Still another object of the present invention is to provide an endoscope offering excellent maneuverability and making it possible to readily achieve accurate observation or treatment.

According to the present invention, there is provided an endoscope having a first bending portion and a second bending portion. The first bending portion is the distal portion of an elongated insertion member. The second bending portion is located at the proximal end of the first bending portion. The dimension of the second bending portion in the longitudinal direction of the insertion member is smaller than the dimension of the first bending portion therein.

According to the present invention, there is provided an endoscope having a first bending portion, a second bending portion, a first control member, and a second control member. The first bending portion is the distal portion of an elongated insertion member. The second bending portion is located at the proximal end of the first bending portion, and the dimension of the second bending portion in the longitudinal direction of the insertion member is smaller than the dimension of the first bending portion therein. The first control member is included in a hand-held unit proximal to the insertion member and used to bend the first bending portion. The second control member is included in the hand-held unit proximal to the insertion member and used to bend the second bending portion.

Other features of the present invention and the advantages thereof will be fully apparent from the description below.

BRIEF DESCRIPTION OF THE DRAWINGS

FIG. 3A is an explanatory diagram showing a bending piece included in the first bending portion;

FIG. 3B is an explanatory diagram showing a bending piece included in the second bending portion;

FIG. 15A is an explanatory diagram showing the insertion member of a conventional enlarged-view endoscope;

FIG. 15B is an explanatory diagram showing the insertion member of a conventional endoscope having two forceps passage channels;

FIG. 15C is an explanatory diagram showing the insertion member of the enlarged-view endoscope shown in FIG. 15A or the endoscope having two forceps passage channels as shown in FIG. 15B, wherein the insertion member has the bending portion shown in FIG. 12;

FIG. 16A shows an explanatory diagram showing the insertion member whose second bending portion is shorter than the first bending portion thereof;

FIG. 16B is an explanatory diagram showing a case where the insertion member shown in FIG. 16A is inserted into a tortuous lumen;

FIG. 18A is an explanatory diagram showing the insertion member whose first bending portion is shorter than the second bending portion thereof;

FIG. 18B is an explanatory diagram showing a case where the insertion member shown in FIG. 18A is inserted in a lumen that is hardly curved;

FIG. 20A is a sectional view showing angulation wire locks included in the second bending portion in order to lock two second wires that are arranged at an Up position and a Right position;

FIG. 20B is a sectional view showing angulation wire locks included in the second bending portion in order to lock two second wires that are arranged at Down and Left positions;

FIG. 20C is a sectional view showing angulation wire locks included in the second bending portion in order to lock two second wires that are arranged at an intermediate position between Up and Right positions and an intermediate position between Down and Left positions;

DESCRIPTION OF THE PREFERRED EMBODIMENTS

An embodiment of the present invention will be described with reference to the drawings below.

FIG. 1 to FIG. 9 are concerned with an embodiment of the present invention.

Figure 1:
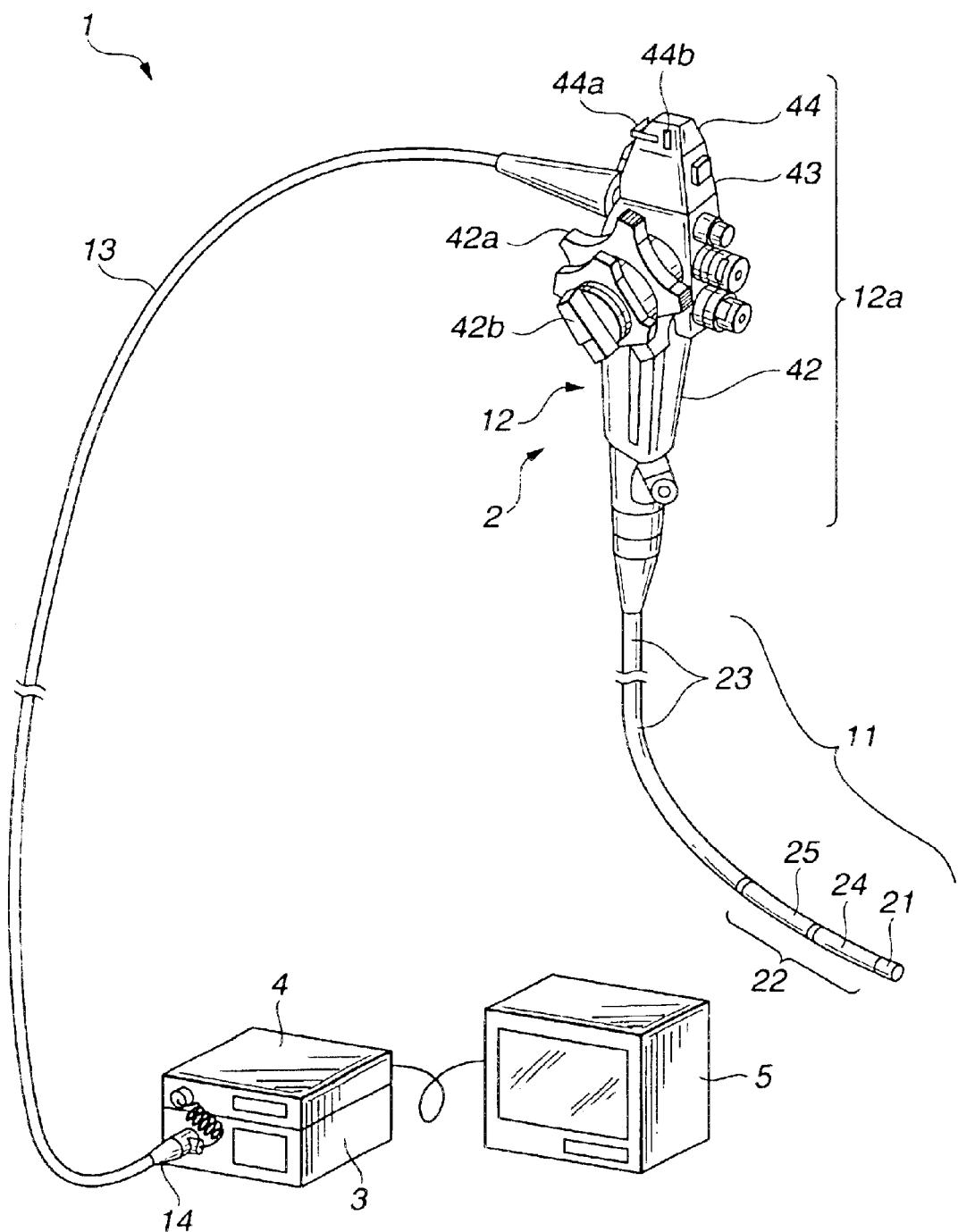
FIG. 1 shows the overall configuration of an endoscope system including an endoscope in accordance with an embodiment of the present invention.

As shown in FIG. 1, an endoscope system 1 having the embodiment of the present invention consists mainly of an electronic endoscope (hereinafter simply an endoscope) 2, a light source apparatus 3, a video processor 4, and a monitor 5. The electronic endoscope 2 has an image pick-up means that is not shown. The light source apparatus 3 is connected to the endoscope 2 so that it can be disconnected freely, and supplies illumination light to the endoscope 2. The video processor 4 is connected to the endoscope 2 so that it can be disconnected freely. The video processor 4 controls the image pick-up means included in the endoscope 2 and processes a signal produced by the image pick-up means to transmit a standard video signal. The monitor 5 displays an endoscopic image according to a signal processed by the video processor 4.

A VTR deck, a video printer, a video disk drive, an image file recording apparatus, or the like, not shown, can be connected to the video processor 4.

The endoscope 2 has an elongated insertion member 11 that is inserted into a region to be observed. A hand-held unit 12 is located at the proximal end of the insertion member 11. The hand-held unit 12 includes a control section 12a that is used to bend first and second bending portions that will be described later.

A universal cord 13 is extended from the lateral side of the hand-held unit 12. A signal cable that is routed to the image pick-up means which is not shown and a light guide over which illumination light is propagated are contained in the universal cord 13.

A connector 14 is attached to the end of the universal cord 13. The connector 14 is coupled to the light source apparatus 3 and connected to the video processor 4 such that it can be connected and disconnected freely.

A distal part 21 is located at the distal end of the insertion member 11. A bending portion 22 capable of freely bending is located at the proximal end of the distal part 21. A flexible-tube 23 is located at the proximal end of the bending portion 22. The flexible tube 23 is formed with an elongated member that is soft and tubular.

An image pick-up unit in which a solid-state image pick-up device that is not shown, such as, a CCD and a circuit board for driving the solid-state image pick-up device are incorporated is included as the image pick-up means in the distal part 21. The distal end of the light guide is extended to the distal part 21, whereby illumination light propagated from the light source apparatus 3 is radiated to a region to be observed in a body cavity. The region to be observed is thus illuminated.

The bending portion 22 is composed of two bending portions, that is, a first bending portion 24 that is the distal half of the bending portion 22 and a second bending portion 25 that succeeds the first bending portion 24.

To begin with, the structure of the bending portion 22 will be described in conjunction with FIG. 2 to FIG. 5.

Figure 2:
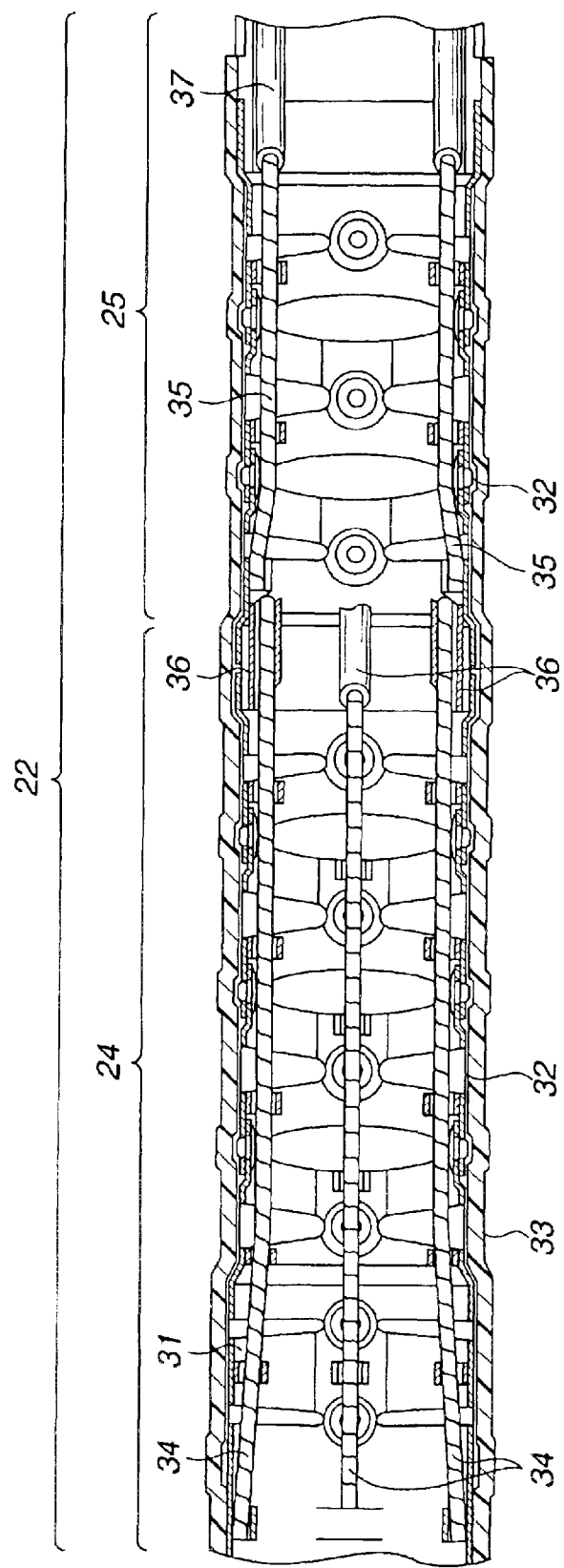
FIG. 2 is a sectional view showing a bending portion of an insertion member included in the endoscope shown in FIG. 1.

As shown in FIG. 2, the first bending portion 24 and second bending portion 25 each has a plurality of bending pieces 31 concatenated so that the bending pieces can rotate freely. The plurality of bending pieces 31 are sheathed with a bending braid 32 made by cylindrically weaving thin wires. The bending braid 32 is sheathed with a bending rubber 33 and thus kept watertight.

The bending braid 32 and bending rubber 33 may be used to sheathe the bending portion 22 composed of the first bending portion 24 and second bending portion 25 over the whole length of the bending portion 22. Otherwise, the first bending portion 24 and second bending portion 25 may be sheathed with the bending braid 32 and bending rubber 33 independently of each other.

First wires 34 used to pull and bend the first bending portion 24 are extended from the distal end of the first bending portion 24.

Second wires 35 used to pull and bend the second bending portion 25 are extended from the distal end of the second bending portion 25.

The first wires 34 are passed through first coil pipes 36 fixed to the distal end of the second bending portion 25, and thus routed to a first control subsection 42, which will be described later, by way of the insertion member 11.

Moreover, the second wires 35 are passed through second coil pipes 37 fixed to the distal end of the flexible tube 23, and thus routed to a second control subsection 44, which will be described later, by way of the insertion member 11.

Furthermore, the thickness of the portion of the bending rubber 33 with which the second bending portion 25 is sheathed is smaller than the thickness of the portion thereof with which the first bending portion 24 is sheathed. Consequently, the second bending portion of the bending portion 22 is more easily bent. Even if a larger number of built-in components must be put in the second bending portion 25, the outer diameter of the second bending portion 25 need not be increased. The ease of bending characterizing the bending portion 22 will therefore not deteriorate.

Generally, when the bending portion 22 is bent, a larger load is often imposed on the second bending portion 25 than on the first bending portion 24. This is because the second bending portion 25 accommodates a larger number of built-in components.

Figure 3A:
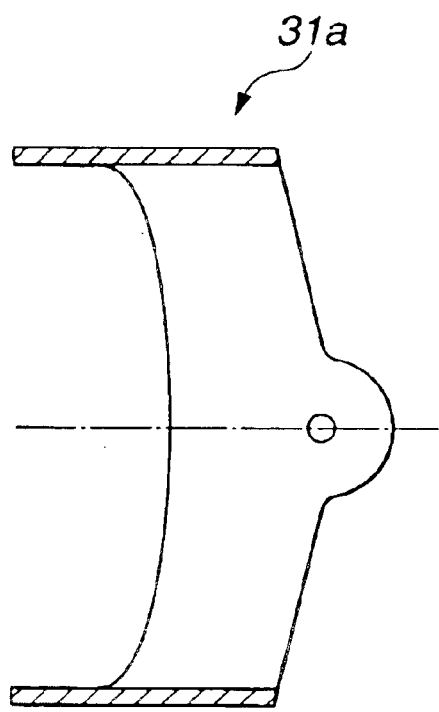
FIG. 3A and FIG. 3B are explanatory diagrams showing bending pieces included in a first bending portion and a second bending portion respectively.
Figure 3B:
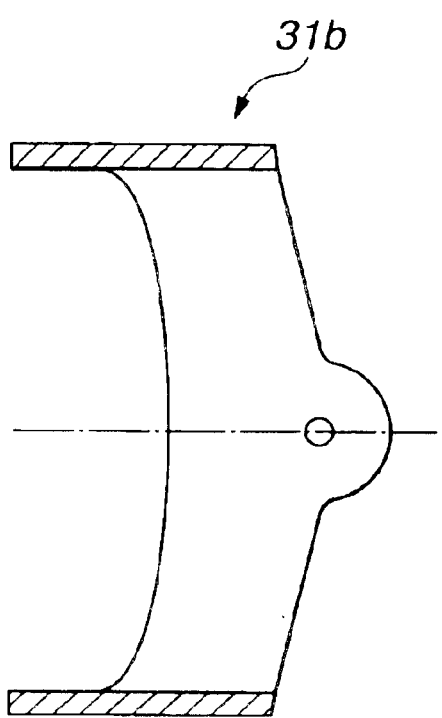

For this reason, the bending pieces 31 constituting the second bending portion 25 of the bending portion 22 are, as shown in FIG. 3A and FIG. 3B, made thicker than those constituting the first bending portion 24.

In other words, bending pieces 31b used to construct the second bending portion 25 of the bending portion 22 as shown in FIG. 3B are made thicker than bending pieces 31a used to construct the first bending portion 24 as shown in FIG. 3A.

Consequently, even when a larger magnitude of force is applied to the second bending portion 25 than to the first bending portion 24, the bending pieces 31 constituting the second bending portion 25 hardly deform. Thus, a bending angle the second bending portion 25 assumes when bent is set will not get smaller than a bending angle it assumes in an initial state.

Figure 4:
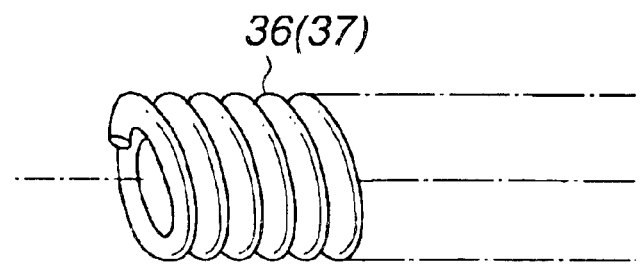
FIG. 4 is an explanatory diagram showing the structure of a coil pipe.

Moreover, coil pipes used as the first coil pipes 36 and second coil pipes 37 are made by, as shown in FIG. 4, finely winding a thin wire so that adjoining portions of the wire will be closely in contact with each other. Owing to this structure, the whole length of the coil pipe may be shortened with application of a load of compression. For this reason, the diameter of a wire used to make the second coil pipes 37 fixed to the proximal end of the second bending portion 25 that must incur a larger load is made larger than the diameter of a wire used to make the first coil pipes 36. Consequently, the second coil pipes 37 are hardly compressed because they are made using a thicker wire than the first coil pipes 36 are. Therefore, even if a larger magnitude of force is applied to the second bending portion 25 than to the first bending portion 24, the coil pipes will not contract. Thus, a bending angle the second bending portion assumes when bent is set will not get smaller than the one it assumes in an initial state.

According to the present embodiment, the control section 12a of the hand-held unit 12 consists of the first control subsection 42 and second control subsection 44. The first control subsection 42 is used to bend the first bending portion 24. The second control subsection 44 is used to bend the second bending portion 25. Owing to the structure, the first bending portion 24 and second bending portion 25 can be bent independently of each other.

Figure 5:
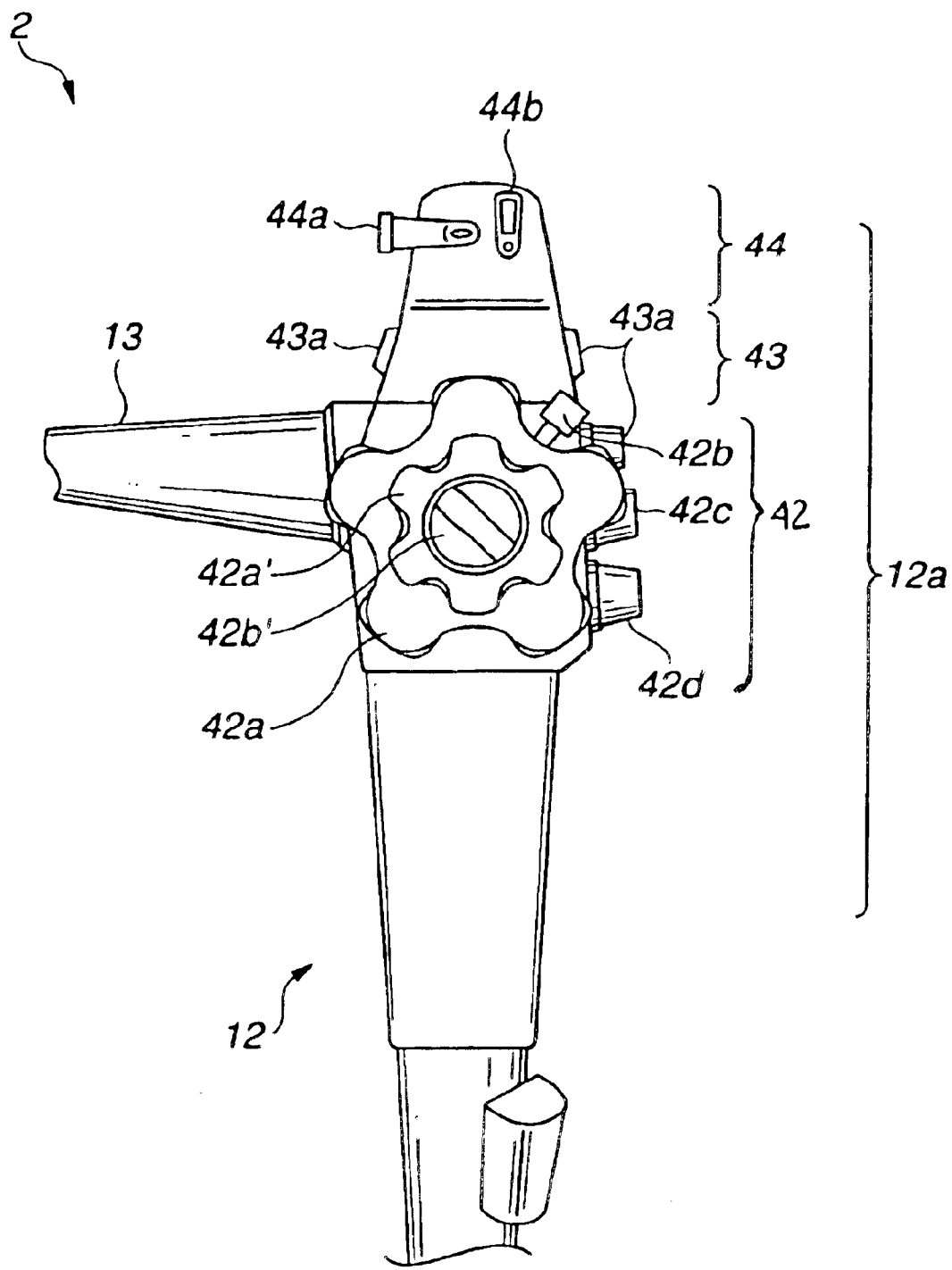
FIG. 5 shows the appearances of a hand-held unit of the endoscope and its surroundings.

The first control subsection 42 includes, as shown in FIG. 5, angling knobs 42a and 42a' and first locking levers 42b and 42b'. The angling knobs 42a and 42a' are used to bend the first bending portion 24. The first locking levers 42b and 42b' are used to lock the angling knobs 42a and 42a' at desired angular positions.

The second control subsection 44 includes, as shown in FIG. 5, a second angling lever 44a used to bend the second bending portion 25 and a second locking lever 44b used to lock the second angling lever 44a at a desired angular position.

The control section 12a has an electric switch subsection 43 that includes remote switches 43a used to instruct the video processor 4 to freeze or unfreeze a view image.

The angling knob 42a is a knob used to bend the first bending portion 24 in Up and Down directions. The angling knob 42a' is a knob used to bend the first bending portion 24 in Right and Left directions.

The first locking lever 42b is a lever used to lock the angling knob 42a at a desired angular position. The first locking lever 42b' is a knob used to lock the angling knob 42a' at a desired angular position.

Furthermore, the first control subsection 42 includes an aeration/perfusion button 42c used to instruct aeration or perfusion and a suction button 42d used to instruct suction.

The endoscope 2 having the foregoing components is used to perform endoscopic examination.

Figure 6:
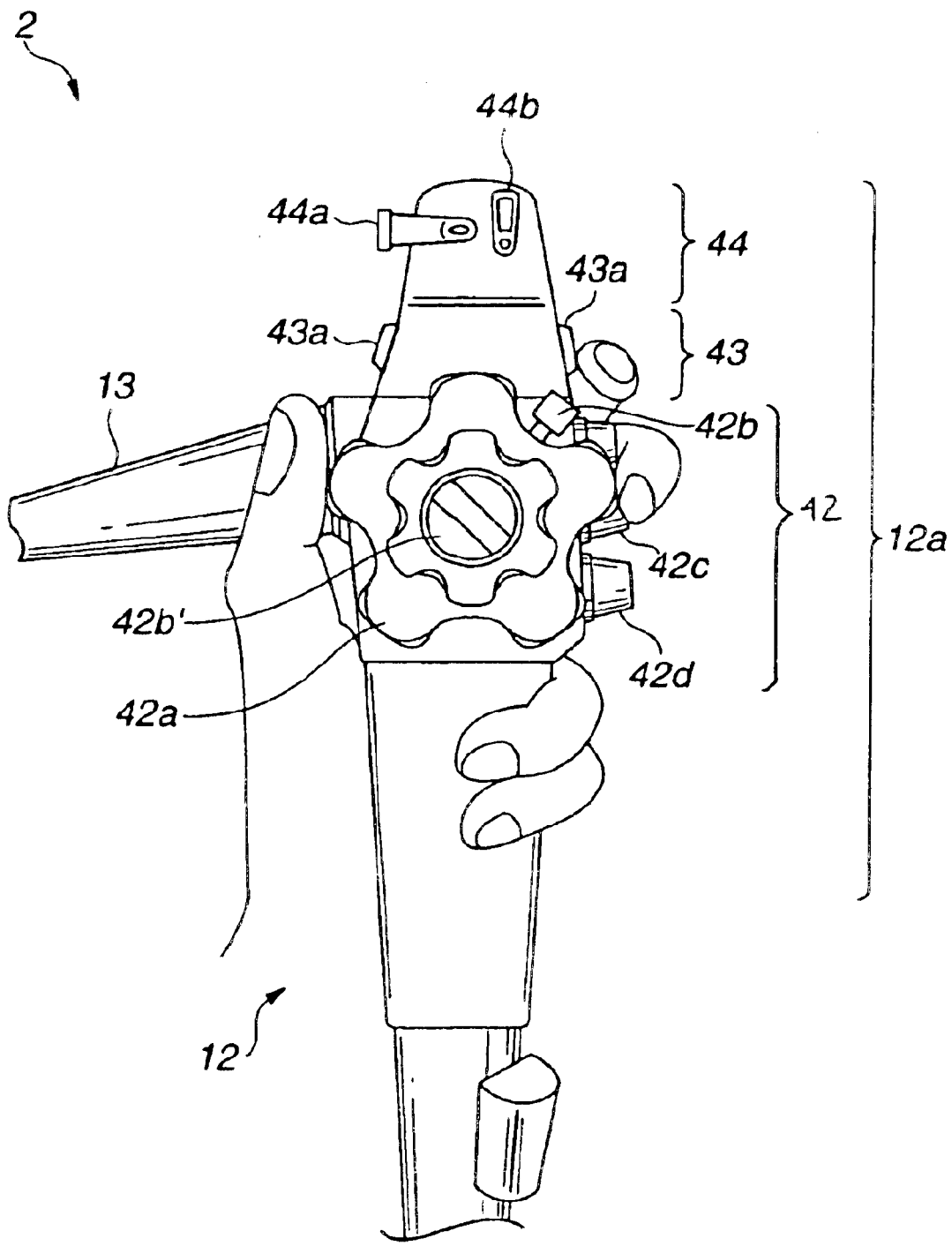
FIG. 6 is an explanatory diagram showing the hand-held unit of the endoscope shown in FIG. 5 and held with a hand.

In general, an operator holds, as shown in FIG. 6, the hand-held unit 12 with his/her left hand so as to angle the endoscope.

In this case, for example, the hand-held unit 12 is borne with the root of the thumb of the left hand and the ring finger and little finger of the left hand. The angling knob 42a and second angling lever 44a are manipulated using the thumb. The index finger and middle finger are also used to manipulate the angling knob 42a and second angling lever 44a when these fingers are not manipulating the remote switches 43a and the buttons including the aeration/perfusion button 42c and suction button 42d.

When an operator wants to bend the first bending portion 24, the operator bears the hand-held unit 12 with the root of the thumb of the left hand and the ring finger and little finger thereof. The operator then manipulates the angling knob 42a using the thumb, index finger, or middle finger thereof. At this time, the angling knob 42a lies within reach of the thumb, index finger, or middle finger.

Moreover, when an operator wants to bend the second bending portion 25, the operator manipulates the second angling lever 44a with his/her right hand that does not hold the hand-held unit 12.

The thumb, index finger, or middle finger may be stretched to a position that is usually beyond reach of it in order to manipulate the second angling lever 44a.

When the remote switches 43a are used or endoscopic treatment is carried out, the first locking levers 42b and 42b, and the second locking lever 44b may be used to lock the angling knobs 42a and 42a, and the second angling lever 44a at desired angular positions. In this case, the thumb can be separated from the hand-held unit, and the endoscope can be manipulated with the insertion member retained in a desired bent state.

Moreover, the second control subsection 44 is separated from the first control subsection 42 with the electric switch subsection 43 between them. When the angling knob 42a is manipulated, the fingers with which the angling knob is manipulated will not come in contact with the second angling lever 44a.

Figure 10A:
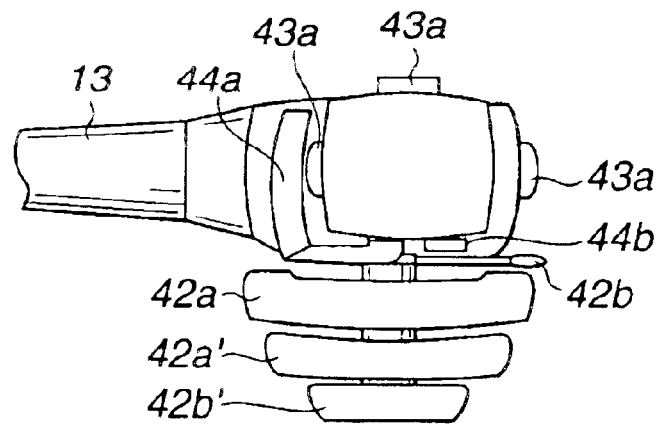
FIG. 10A to FIG. 10C are plan views showing other examples of an angling knob included in the second control subsection.

The second angling lever 44a may be, as shown in the plan view of FIG. 10A, jutted out in a direction opposite to the direction of the angling knobs 42.

Figure 10B:
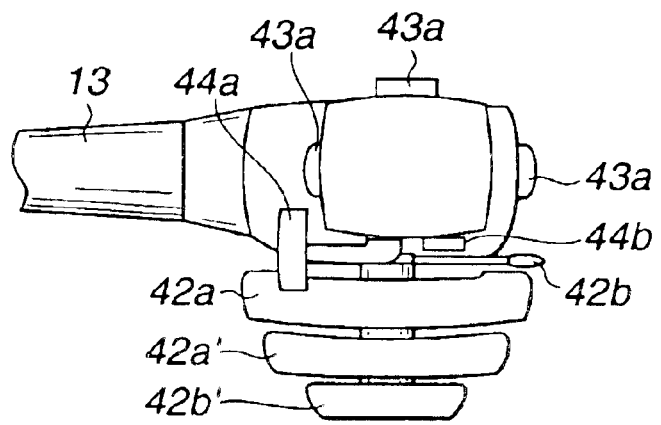
Figure 10C:
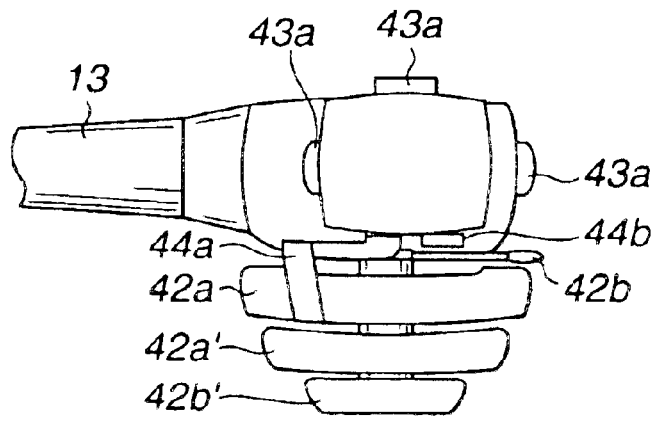

The foregoing structure may be modified in consideration of ease with which the second angling lever 44a can be manipulated with, for example, the right hand, so that the second angling lever 44a will jut out towards the angling knobs 42 as shown in FIG. 10B and FIG. 10C.

Figure 7:
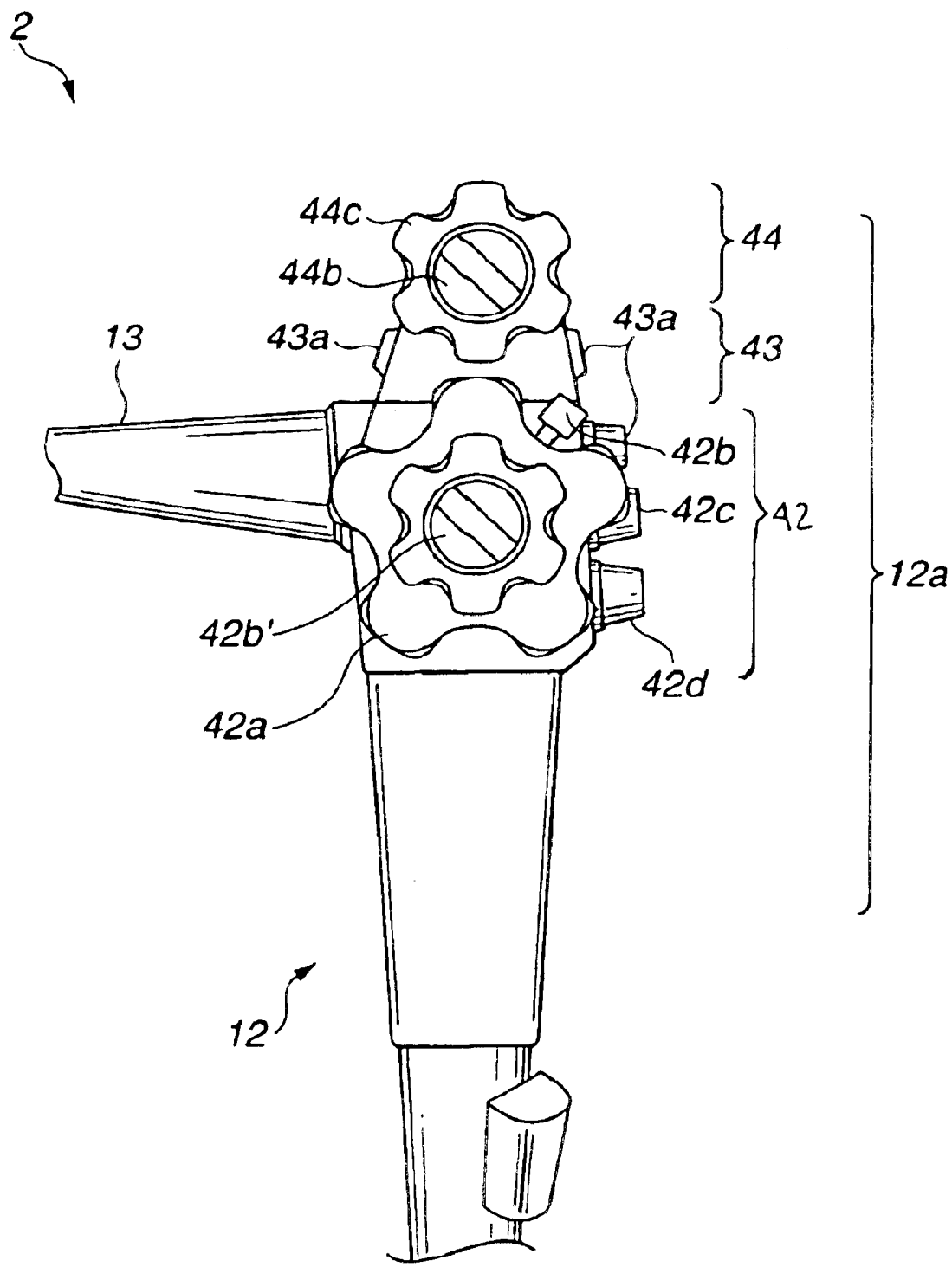
FIG. 7 shows the appearance of a hand-held unit of an endoscope that has an angling knob, which is used to manipulate the second bending portion, included in a second control subsection, and the appearance of its surroundings.

Referring to FIG. 5 and FIG. 6, the second angling lever 44a that is a lever used to bend the second bending portion 25 is included in the second control subsection 44. However, the present invention is not limited to the second angling lever 44a. As shown in FIG. 7, when the second bending portion can be bend in freely selected directions, an angling knob 44c that resembles the angling knob 42a may be substituted for the second angling lever 44a.

Figure 8:
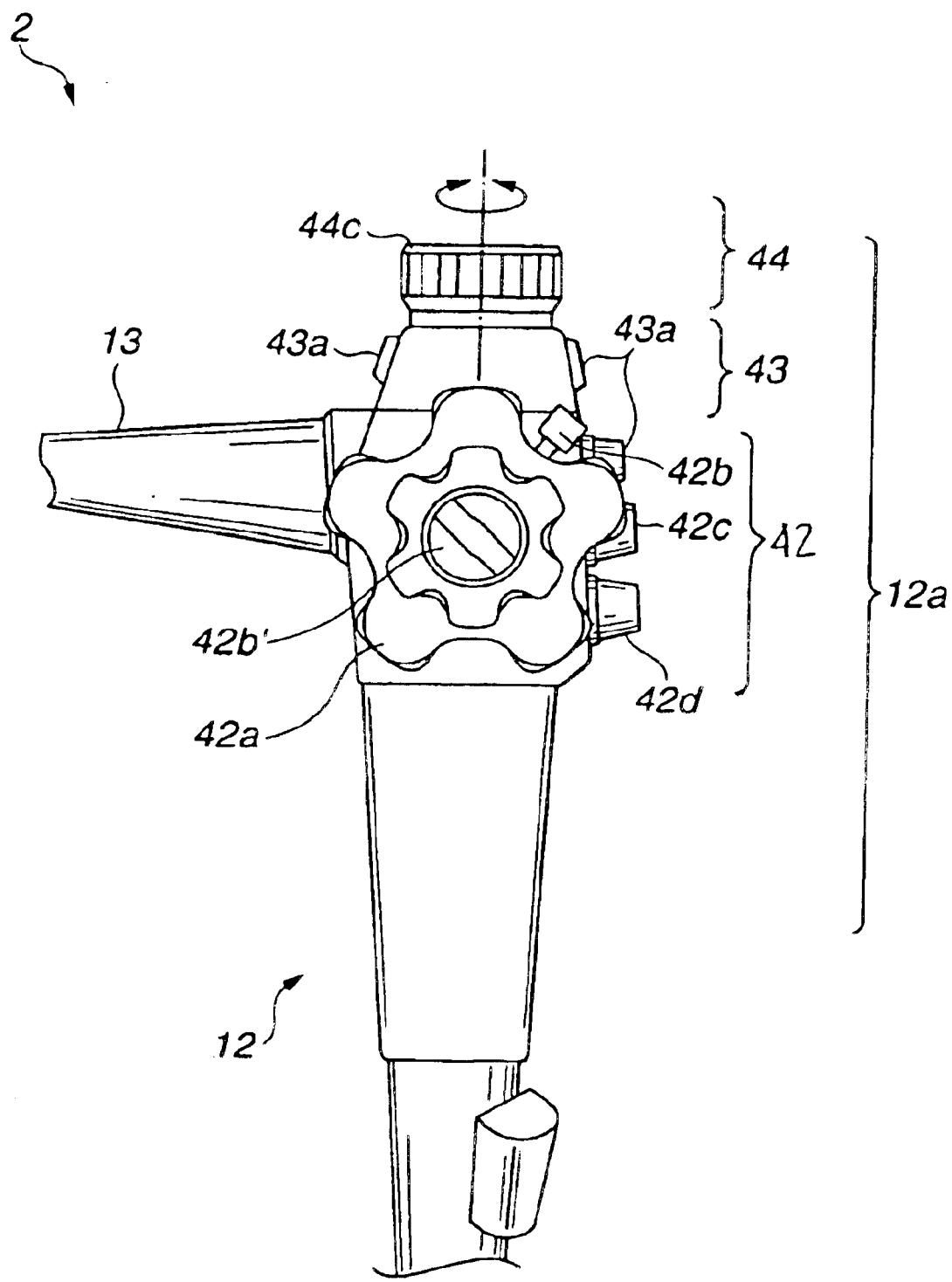
FIG. 8 shows the appearance of a hand-held unit of an endoscope having a first control subsection and a second control subsection in which the axes of rotation cross at a right angle, and the appearance of the surroundings of the hand-held unit.

The axes of rotation in the first control subsection 42 and second control subsection 44 may extend parallel to each other as shown in FIG. 5. Alternatively, the axes of rotation may meet at an angle as shown in FIG. 8. Referring to FIG. 8, the axes of rotation in the first control subsection 42 and second control subsection 44 cross at right angles.

Figure 9:
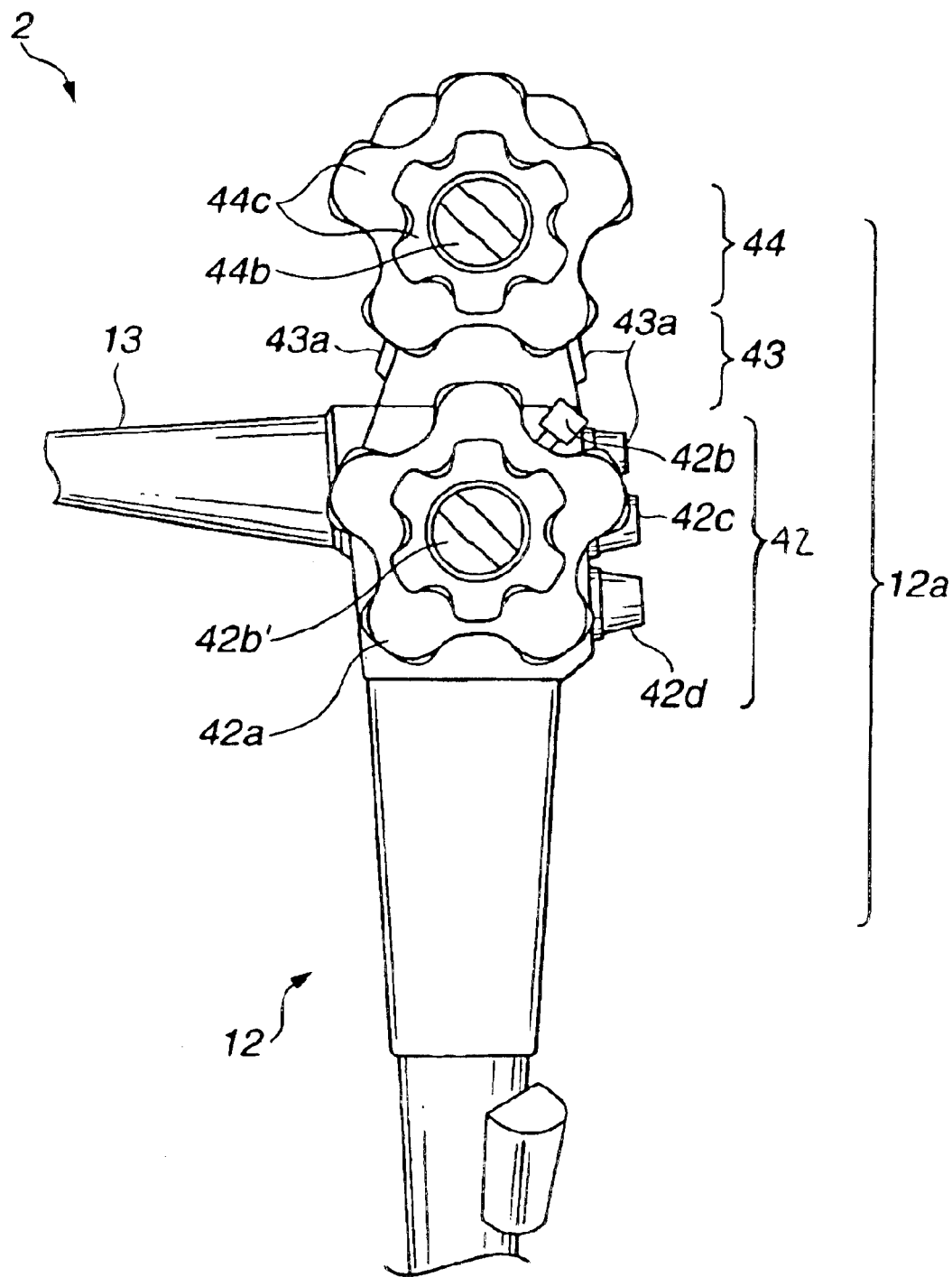
FIG. 9 shows the appearance of a hand-held unit of an endoscope that has two angling knobs included in a second control subsection, and the appearance of its surroundings.

Moreover, when the second bending portion 25 is designed to be able to bend in four directions, the second control subsection 44 includes two angling knobs 44c as shown in FIG. 9. The second bending portion 25 can thus be bent in four directions.

Consequently, in the endoscope 2 in accordance with the present embodiment, the first and second bending portions 24 and 25 can be bent independently of each other. The two bending portions can be handled in the same manner as an ordinary bending portion is. The endoscope 2 of the present embodiment offers improved ease of bending.

The endoscope 2 of the present embodiment has the second control subsection 44 separated from the first control subsection 42. Consequently, when the first control subsection 42 alone is used, the second control subsection will not annoy an operator. The endoscope offers ease of bending of the same level as a normally employed endoscope having one bending portion does.

Furthermore, the endoscope 2 of the present embodiment has the second control subsection 44 and first control subsection 42 separated from each other with the electric switch subsection 43 between them. Consequently, the maneuverability offered by the endoscope will not be poorer than the maneuverability offered by an ordinary endoscope. In addition, when the first control subsection 42 and electric switch subsection 43 are used, the second control subsection 44 will not be manipulated incorrectly.

In the endoscope 2 of the present embodiment, the axes of rotation in the first control subsection 42 and second control subsection 44 meet at an angle. Consequently, when the first control subsection 42 is held with one hand and the second control subsection 44 is manipulated with the other hand, the second control subsection 44 can be manipulated easily.

The endoscope 2 in accordance with the present embodiment is an electronic endoscope having the image pick-up unit incorporated in the distal part 21 of the insertion member 11. Alternatively, the present invention may be implemented in an electronic endoscope in which an image guide that is not shown is run through the insertion member 11 and an object image propagated along the image pick-up guide is picked up by an image pick-up unit incorporated in the control section 12a. Moreover, the present invention may be implemented in a so-called optical endoscope in which an object image propagated along the image guide is viewed through an eyepiece unit mounted on the control section 12a. In any case, the endoscope has the bending portion 22 composed of the first bending portion 24 and second bending portion 25.

The present invention is not limited to the aforesaid embodiment, but can be modified in various aspects with the gist of the present invention left unchanged.

Figure 11:
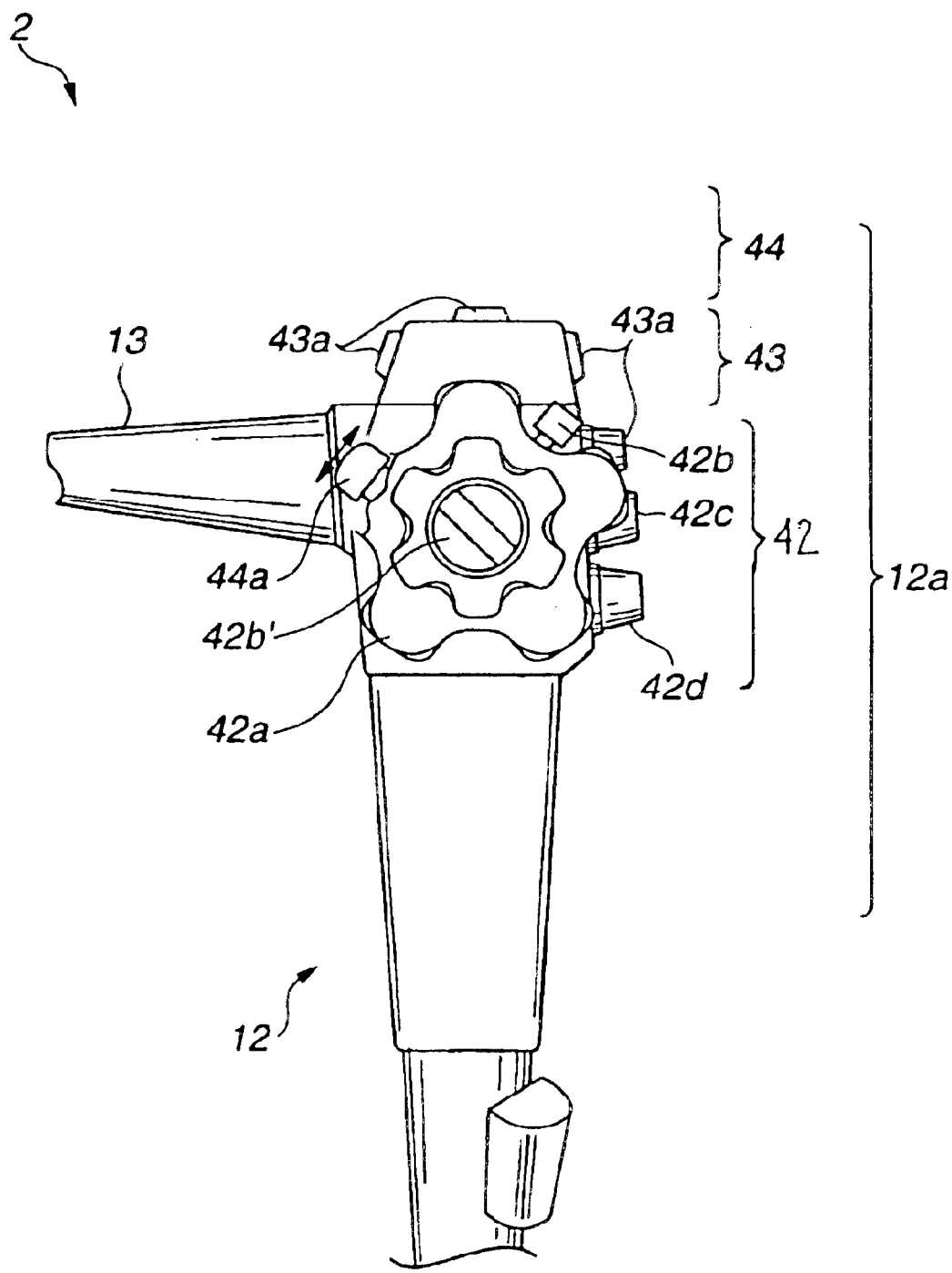
FIG. 11 shows the appearance of another example of the angling knob included in the second control subsection.

For example, as shown in FIG. 11, the second angling lever 44a may be located at a position at which a forceps lift lever is usually-located in an ordinary endoscope.

As far as observation of an intracavitary region is concerned, observing a region to be observed from the front side thereof is very helpful in a viewpoint of producing a clear image devoid of deformation.

When an endoscope has the same structure as the aforesaid one, that is, the elongated insertion member 11 has the bending portion 22 composed of the first bending portion 24 and second bending portion 25, the first bending portion 24 and second bending portion 25 are bent independently of each other. Thus, the distal part 21 of the insertion member can be faced a region to be observed.

Figure 21:
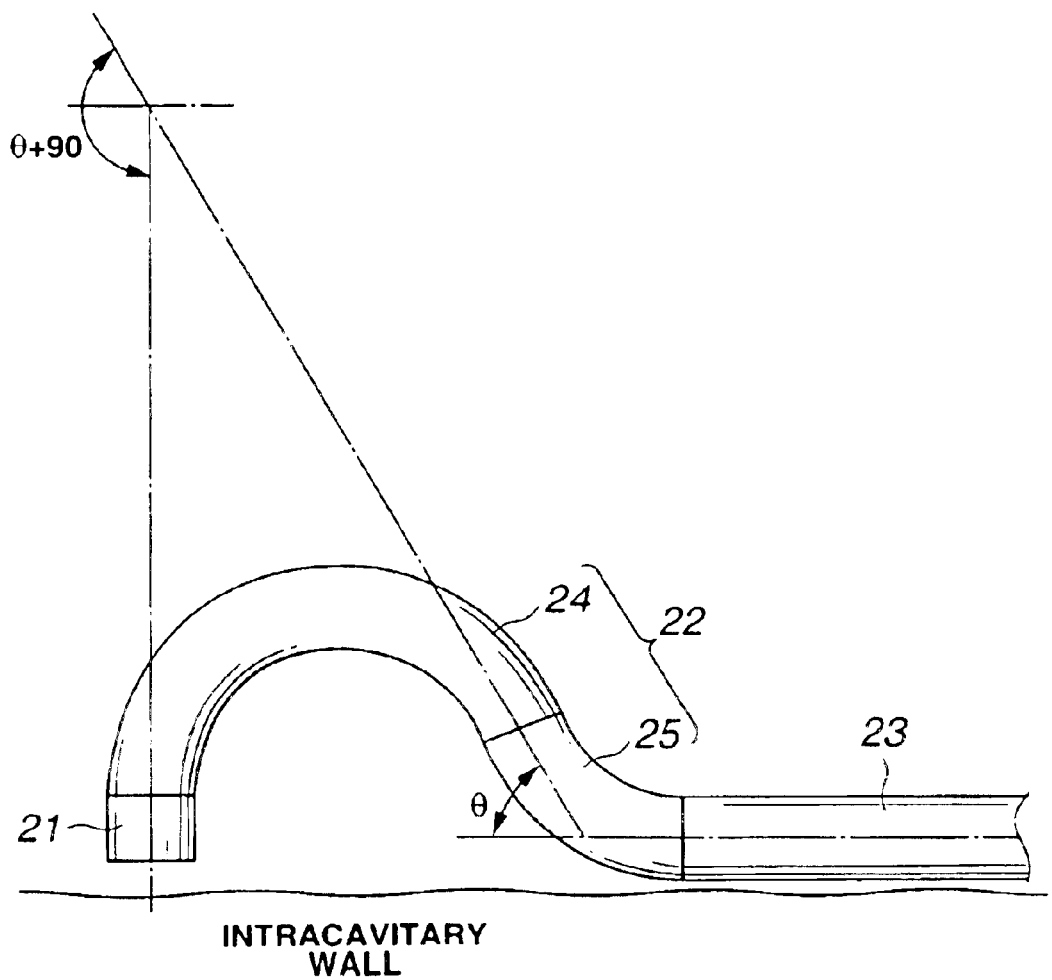
FIG. 21 is an explanatory diagram showing the insertion member of a conventional endoscope whose bending portion is composed of a first bending portion and a second bending portion.

For example, the insertion member 11 may be in close contact with the intracavitary wall as shown in FIG. 21. In this case, the second bending portion 25 is bent upward by an angle θ with respect to the longitudinal axis of the insertion member 11. At the same time, the first bending portion 24 is bent downwards by an angle θ+90° with respect to the longitudinal axis of the insertion member 11. Consequently, the distal part 21 of the insertion member 11 is angled to face a region to be observed that is located on an intracavitary wall.

FIG. 21 is an explanatory diagram showing the insertion member of a conventional endoscope having a bending portion composed of a first bending portion and a second bending portion.

However, assume that the insertion member 11 is in close contact with an intracavitary wall, and that the distal part 21 of the insertion member is faced the intracavitary wall. In this case, the distal part 21 is located near an extension of the longitudinal axis of the flexible tube 23 (which is in close contact with the intracavitary wall) of the insertion member 11. Consequently, the distal part 21 cannot have a predetermined distance from the region to be observed.

If the distal part 21 cannot be separated from a region to be observed by a predetermined distance, it is hard to observe the region to be observed during endoscopic examination. Although the predetermined distance cannot be preserved, if an attempt is made to perform endoscopic treatment, a therapeutic instrument or the like may not be able to be projected from the distal part 21 towards an intracavitary wall. Consequently, the endoscopic treatment fails.

In order to solve the above problem, it is conceivable to increase the dimension of the second bending portion 25. The second bending portion 25 is bent appropriately in order to raise the first bending portion 24 relative to the intracavitary wall, whereby the predetermined distance may be preserved. However, this structure has a drawback that the overall length of the bending portion 22 is too large.

The bending portion 22 has, as described in conjunction with FIG. 2, the plurality of bending pieces 25 sheathed with the braid 32 and bending rubber 33. The surface of the bending portion 22 is therefore finely irregular and hardly smooth. The bending portion 22 must therefore have a minimum necessary length.

There is therefore a long-persistent demand for an endoscope that offers improved ease of observation and treatment when the distal part 21 is faced an intracavitary wall with both the first bending portion 24 and second bending portion 25 bent.

Referring to FIG. 12 to FIG. 20C, an example of the structure of an endoscope including two bending portions will be described below.

FIG. 12 to FIG. 20C show the example of the structure of an endoscope including two bending portions.

Figure 12:
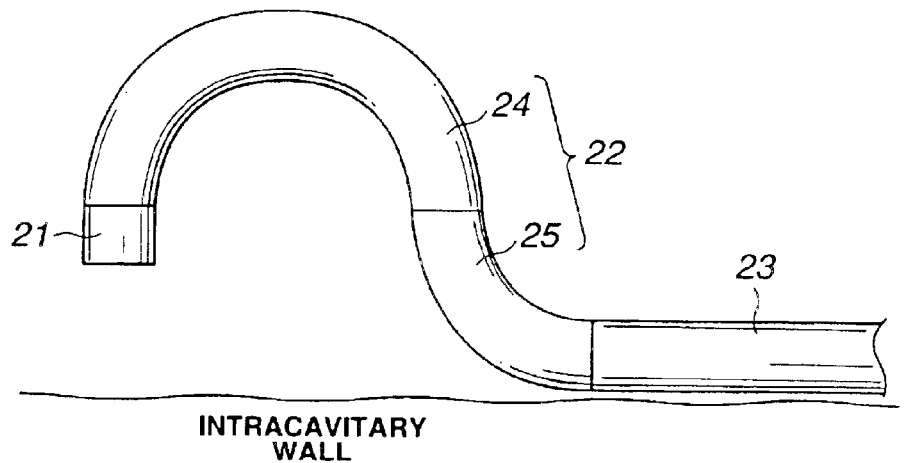
FIG. 12 is an explanatory diagram showing an insertion member having a bending portion composed of a first bending portion and a second bending portion by which bending angles are assumed when bent are set.

As shown in FIG. 12, the first bending portion 24 and second bending portion 25 are bent, and the distal part 21 of the insertion member is thus angled in a direction perpendicular to the longitudinal axis of the insertion member 11, that is, faced an intracavitary wall. In this state, bending angles the first bending portion 24 and second bending portion 25 that constitute the bending portion 22 assume when bent is set are determined so that the distal part 21 will always lie above an extension of the longitudinal axis of the insertion member 11 (so that the distal part 21 can be distanced from a region to be observed).

Referring to FIG. 12, the bending angle the second bending portion 25 assumes when bent, θ, is set substantially to 90° and the bending angle the first bending portion 24 assumes when bent, (θ+90°), is set substantially to 180°.

Figure 15A:
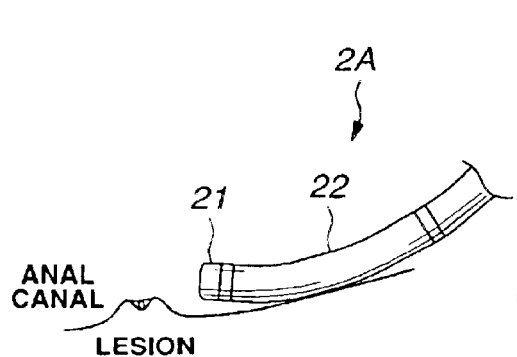
FIG. 15A to FIG. 15C are explanatory diagrams showing the bending portion shown in FIG. 12 and adapted to other endoscopes.

The thus-structured bending portion 22 is adapted to a conventional enlarged-view endoscope 2A that has, as shown in FIG. 15A, an image pick-up unit (not shown), of which focus can be changed from one to another, incorporated in the distal part 21. Otherwise, the bending portion 22 is adapted to a conventional endoscope 2B having, as shown in FIG. 15B, two forceps passage channels 51.

As shown in FIG. 15A, the conventional enlarged-view endoscope 2A has the insertion member 11 that includes one bending portion. Therefore, the distal part 21 is located on or near an extension of the longitudinal axis of the flexible tube 23 (that is in close contact with an intracavitary wall) along the intracavitary wall. It is therefore hard to observe a lesion located tangentially to the intracavitary wall.

Figure 15B:
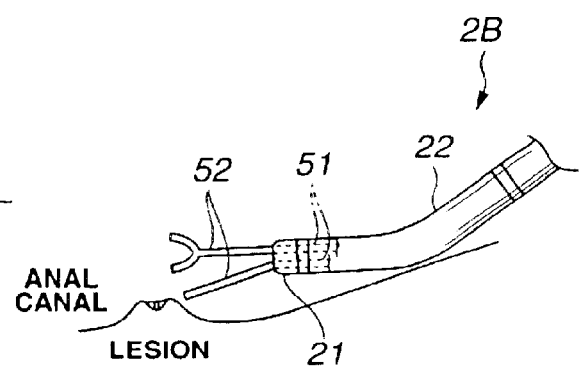

Referring to FIG. 15B, a predetermined distance cannot be preserved between the distal part 21 of the insertion member of the endoscope 2B having two forceps passage channels 51 and a region to be observed. A therapeutic instrument 52 or the like cannot be projected from the distal part 21. It is therefore hard to perform endoscopic treatment.

Figure 15C:
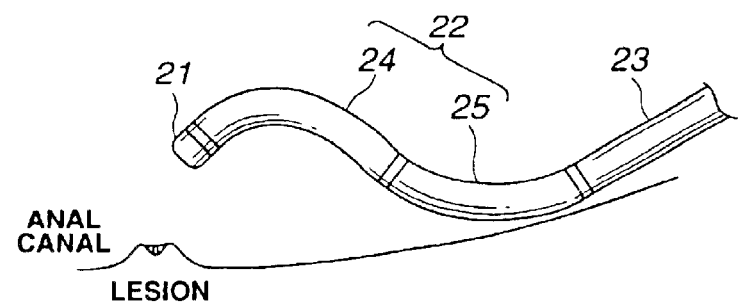

Now, when the bending portion 22 is structured as shown in FIG. 12, the distance between the distal part 21 and a region to be observed can be adjusted as shown in FIG. 15c. Moreover, two therapeutic instruments can be used for endoscopic treatment.

Figure 13:
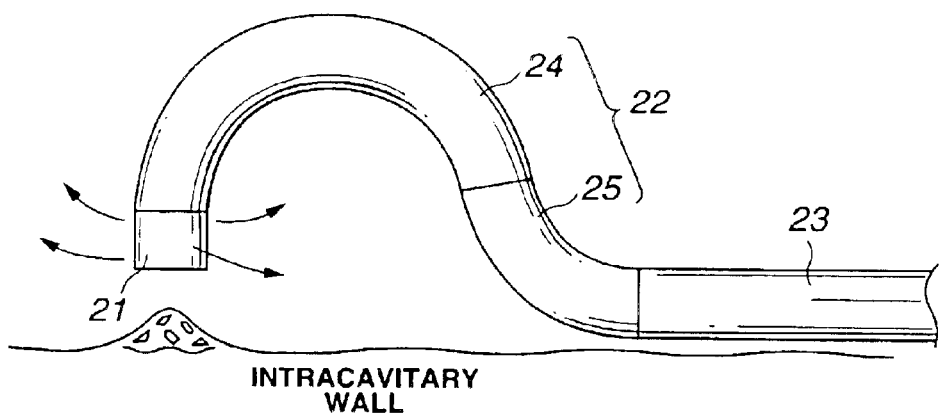
FIG. 13 is an explanatory diagram showing movements made by the insertion member shown in FIG. 12.

As shown in FIG. 13, when a lesion is observed, the first bending portion 24 and second bending portion 25 are bent, and the second locking lever 44b is manipulated in order to lock the second angling lever 44a at a desired angular position. Consequently, the second bending portion 25 can be retained in a desired bent state. The first bending portion 24 is bent vertically and laterally with the second angling-lever 44a locked. Eventually, the distal part of the endoscope can be angled in the directions of arrows with the lesion and distal part distanced from each other.

In short, observation can be continued with the relative positions of the lesion and the distal part varied.

Figure 14:
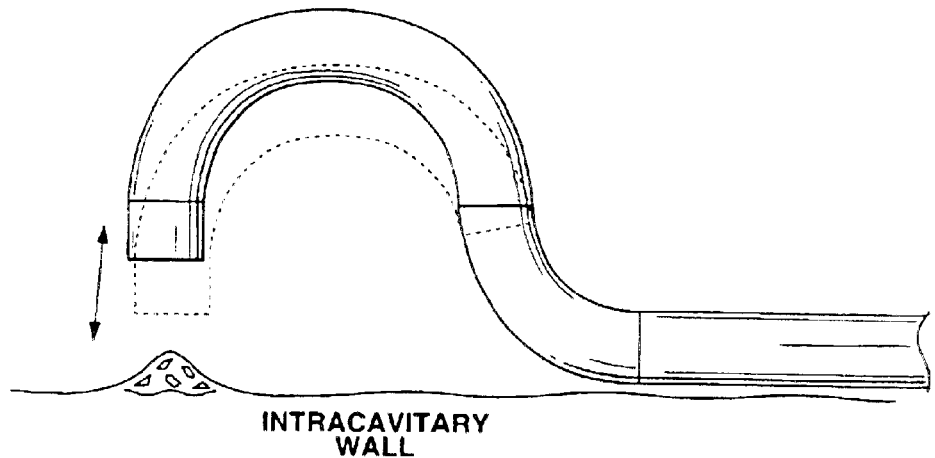
FIG. 14 is an explanatory diagram showing other movements made by the insertion member shown in FIG. 12.

Furthermore, as shown in FIG. 14, the first locking levers 42b and 42b' are manipulated to lock the bending knobs 42 at desired angular positions. Consequently, the first bending portion 24 is retained in a desired bent state. In this state, the second bending portion 25 is bend in two directions. Thus, the distal part of the endoscope can be angled in the directions of arrows while faced the lesion.

In short, the distance between the lesion and the distal part of the endoscope can be adjusted with the distal part angled to the lesion.

As shown in FIG. 13 and FIG. 14, the first bending portion 24 and second bending portion 25 can be retained in respective bent states. This leads to improved ease of manipulation offered for endoscopic observation.

Figure 16A:
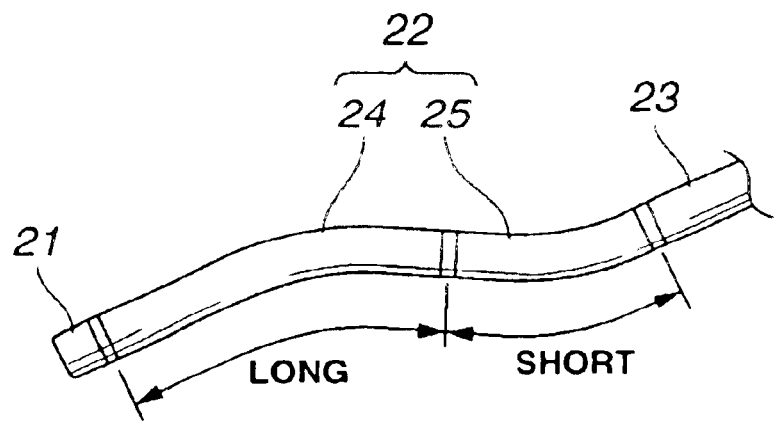
FIG. 16A and FIG. 16B are explanatory diagrams showing an insertion member that has a second bending portion thereof made shorter than a first bending portion thereof.
Figure 16B:
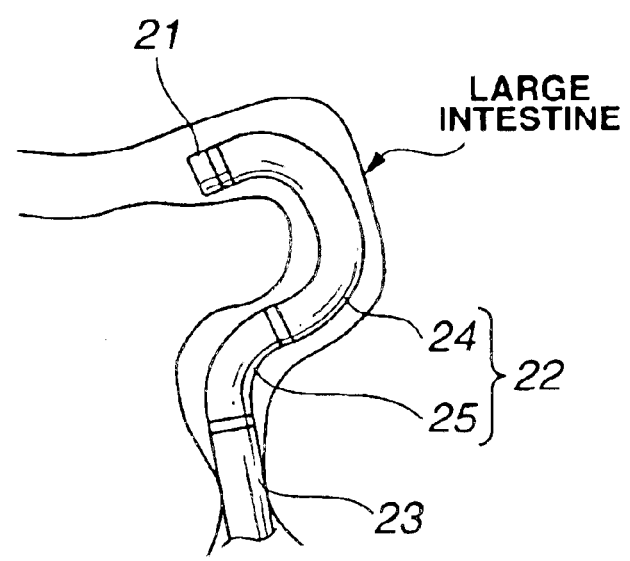

Furthermore, the bending portion 22 may be designed such that the second bending portion 25 will be shorter than the first bending portion 24 as shown in FIG. 16A. For example, when the endoscope is used to observe a tortuous lumen such as the lumen of the large intestine, even if the second bending portion 25 is bent, the second bending portion 25 will not interfere with the intestinal wall but the bending portion 22 can be entirely moved.

Figure 18A:
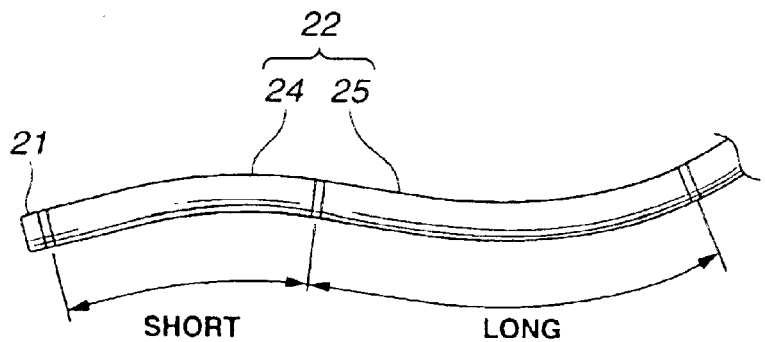
FIG. 18A and FIG. 18B are explanatory diagrams showing an insertion member that has a first bending portion thereof made shorter than a second bending portion thereof.
Figure 18B:
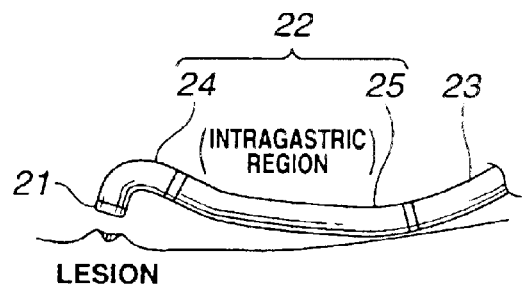

In contrast with FIG. 16A, FIG. 18A shows the bending portion having the second bending portion 25 made longer than the first bending portion 24. As shown in FIG. 18B, when the bending portion is inserted in a lumen that is almost not at all curved, for example, the lumen of the stomach, ease of insertion or treatment can be improved. Namely, a therapeutic instrument can be inserted easily during endoscopic treatment, or the distal part 21 of the insertion member can be angled easily finely.

Figure 17B:
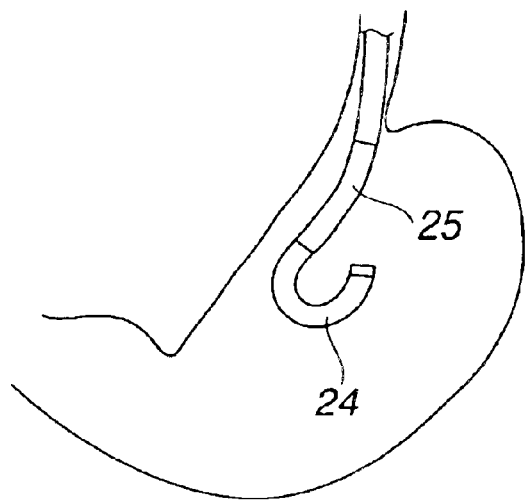
FIG. 17A to FIG. 17C are explanatory diagrams showing a case where an endoscope is used to observe the cardia of the stomach and its surroundings.
Figure 17C:
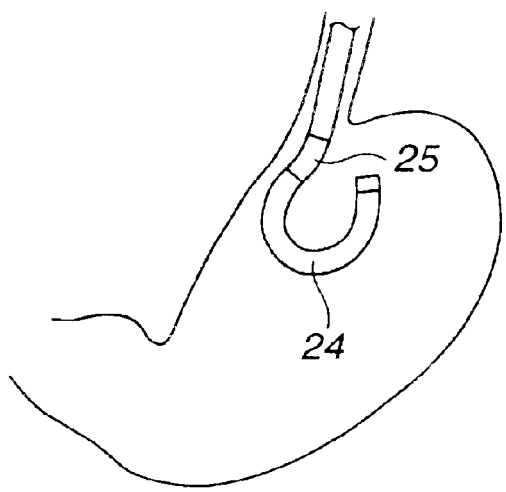
Figure 17A:
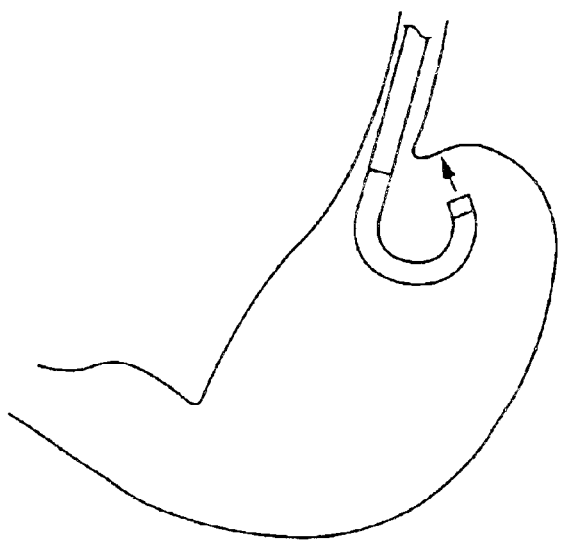

As shown in FIG. 17A, when an endoscope has only one bending portion, the bending portion can be bent in order to position the distal part closely to the cardia of the stomach. However, the cardia and its surroundings are observed obliquely. It is therefore hard to view the cardia and its surroundings from the front sides thereof.

As shown in FIG. 17B, when the second bending portion 25 is somewhat long, since the second bending portion 25 must be fully jutted out of the esophagus, the first bending portion 24 recedes from the cardia of the stomach. Therefore, even if an attempt is made to bend the first bending portion in order to observe the cardia and its surroundings, the distance between the distal part of the endoscope and the cardia is too large to achieve observation successfully.

Now, in an endoscope shown in FIG. 17C, the dimension of the second bending portion 25 in a direction of insertion is smaller than the dimension of the first bending portion 24 therein. When the dimensions of the first and second bending portions 24 and 25 in the direction of insertion are thus set, if the first and second bending portions 24 and 25 are bent in order to observe the cardia of the stomach and its surroundings, the distal part of the endoscope can be positioned closely to the cardia. This results in successful observation.

Figure 19:
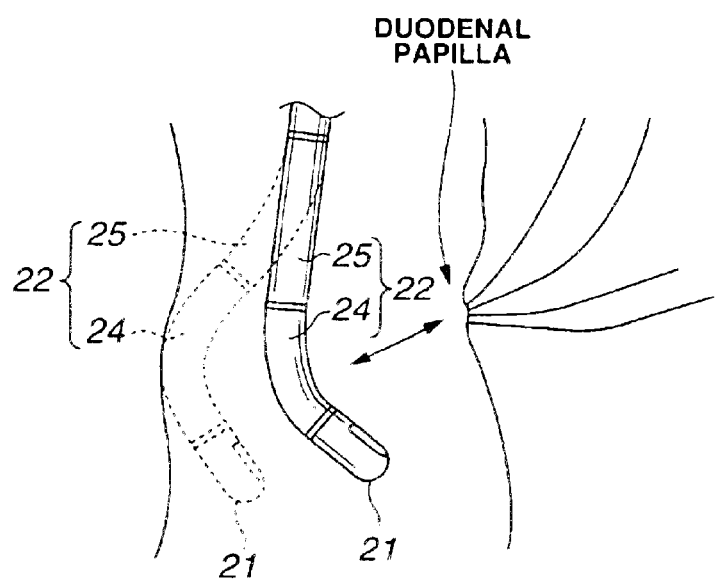
FIG. 19 is an explanatory diagram showing a case where an insertion member characterized in that the number of the directions in which a second bending portion thereof is bent is limited to a minimum necessary number of directions is inserted in a lumen in which only a specific object can be observed.

As shown in FIG. 19, an endoscope may be used exclusively to observe, for example, the duodenum. In this case, the second bending portion 25 is made bendable in only one direction (an Up or Down direction). Like this, the number of the bendable directions of the second bending portion 25 is limited to a minimum necessary number of directions. This leads to a simplified angling mechanism.

FIG. 19 shows a case where the distal part 21 of the insertion member is made to approach the duodenal papilla.

When the duodenal papilla or any other region of the duodenum is incised, the distal end of an endoscope should be made to approach obliquely for more successful treatment.

Figure 20A:
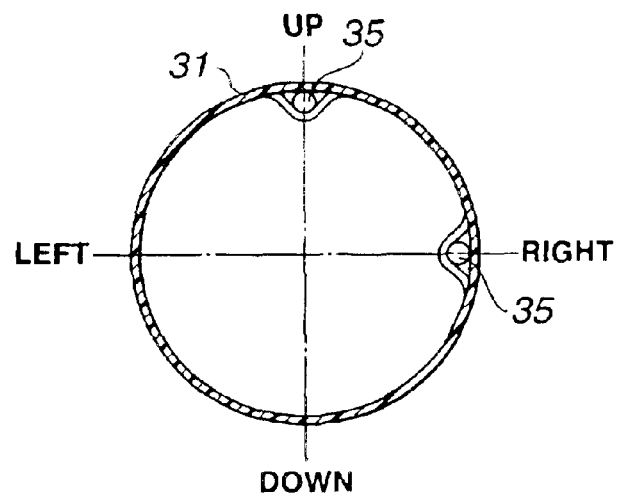
FIG. 20A to FIG. 20C are explanatory diagrams showing angulation wires that are arranged at positions in the second bending portion that ensure easy bending in oblique directions.
Figure 20B:
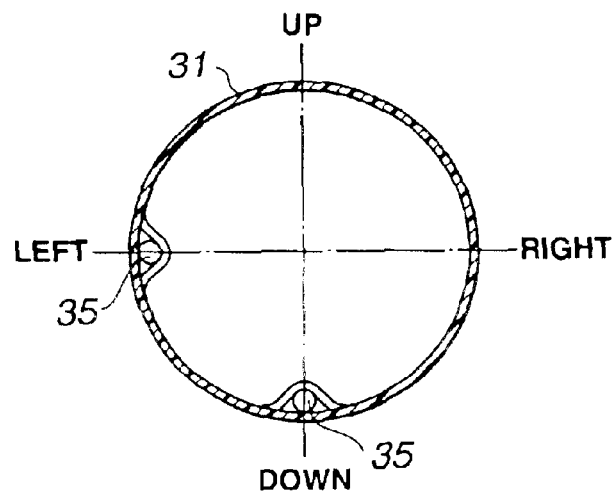
Figure 20C:
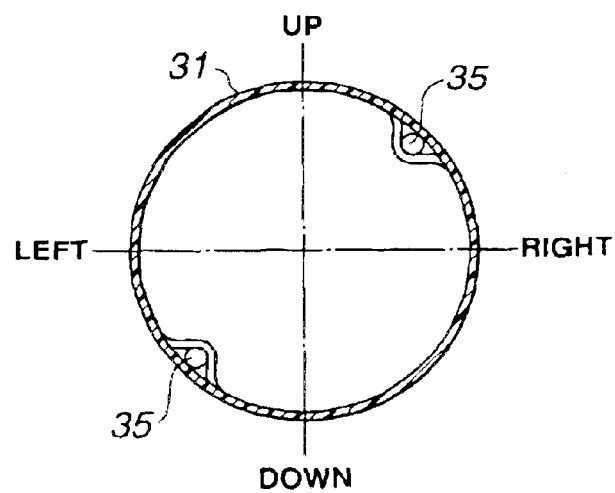

In this case, the second wires 35 to be pulled in order to bend the second bending portion 25 may be arranged as shown in FIG. 20A to FIG. 20C.

As shown in FIG. 20A and FIG. 20B, the second wires 35 lying through the second bending portion 25 may be arranged at Up and Right positions or Down and Left positions so that the second bending portion 25 can be easily bent obliquely.

As shown in FIG. 20C, the second wires 35 lying through the second bending portion 25 may be arranged at an intermediate position between the Up and Right positions and an intermediate position between the Down and Left positions.

As far as the aforesaid endoscope whose elongated insertion member 11 has the bending portion 22 is concerned, the second bending portion 25 of the bending portion 22 is first bent. Namely, the one of the second wires 35 described in conjunction with FIG. 2, which is located at the Up position, is pulled in order to bend the second bending portion 25 in the Up direction. If the second bending portion 25 is straightened thereafter, since restoring force exerted by the bending rubber 33 with which the second bending portion 25 is sheathed is weak, the one of the second wires 35 which is located at the Down position must be pulled. Therefore, an angling mechanism is very complex.

There is therefore a demand for an endoscope having a simple structure and having the second bending portion 25 capable of being straightened.

Figure 22:
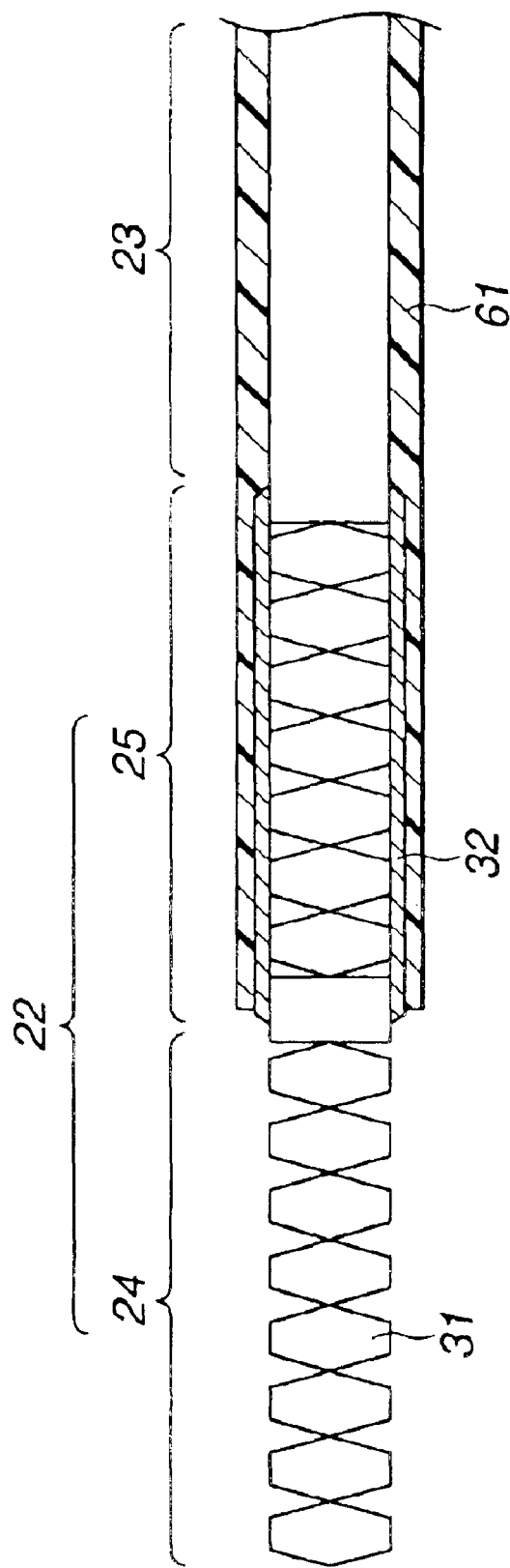
FIG. 22 is a schematic explanatory diagram showing an insertion member whose bending portion includes a second bending portion that can be straightened.
Figure 23:
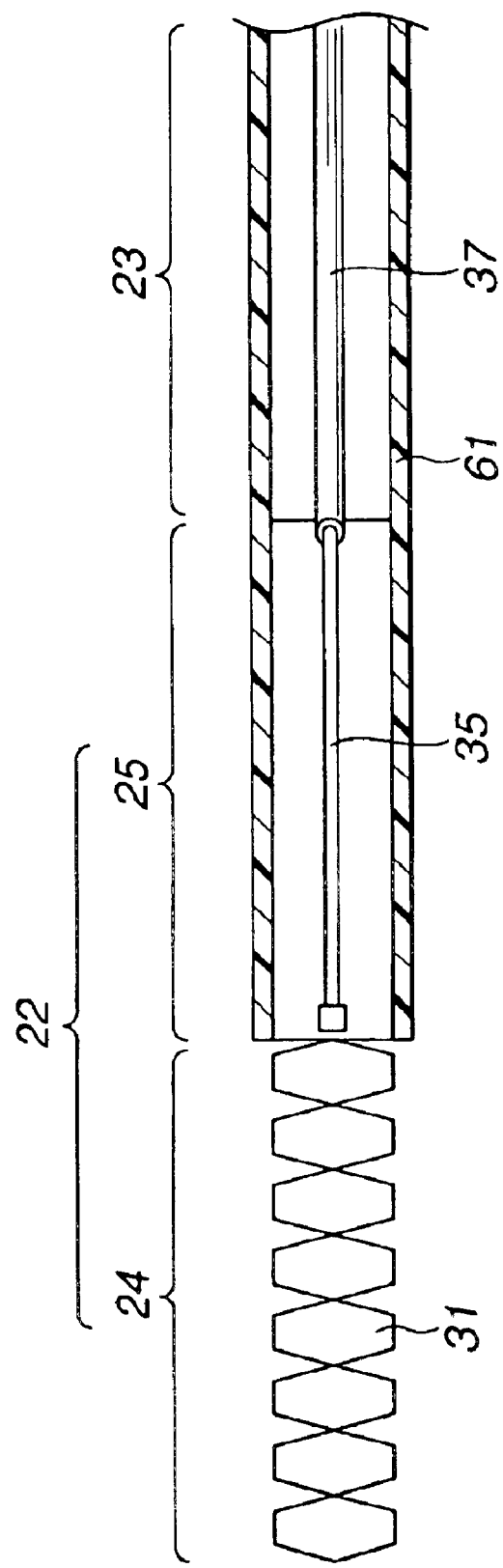
FIG. 23 is a schematic explanatory diagram showing an insertion member that is a variant of the insertion member shown in FIG. 22.

Referring to FIG. 22 and FIG. 23, an example of the structure of an endoscope whose second bending portion can be straightened will be described below.

As shown in FIG. 22, the first bending portion 24 of the bending portion 22 has a plurality of bending pieces 31 concatenated so that the bending pieces can rotate freely. The concatenated bending pieces 31 are sheathed with the bending braid 32 made by cylindrically weaving thin wires, and then covered with the bending rubber 33.

The second bending portion 25 has, similarly to the first bending portion 24, the plurality of bending pieces 31 concatenated so that the bending pieces can rotate freely. The bending pieces 31 are sheathed with the bending braid 32. The bending braid 32 is coated with a resilient resin 61 such as polyester which is the same resin as that adopted for the flexible tube 23.

Consequently, the second bending portion 25 has the bending braid 32 coated with the resilient resin 61 that is the same resin as that adopted for the flexible tube 23. Therefore, the second bending portion 25 that has been bent can be straightened by merely slackening one of the second wires 35. Namely, the second wire 35 to be slackened is a second wire that has been pulled in order to bend the second bending portion 25 in a direction that runs externally parallel to the second wire.

Moreover, the second wires 35 used to bend the second bending portion 25 may lie, as shown in FIG. 23, alone at one position, so that the second bending portion 25 can be bent in only one direction.

As described in conjunction with FIG. 2, the second wires 35 are passed through the second coil pipes 37 inside the flexible tube 23 up to the proximal end of the second bending portion 25.

The second bending portion 25 has the same structure as, for example, the flexible tube 23 (for example, as shown in FIG. 22, molded using the same resin 61 as that adopted for the flexible tube 23). Thus, the second bending portion 25 is easily straightened.

Consequently, when the second wires 35 are not tensioned, the second bending portion 25 is automatically straightened. Only one of the second wires 35 can therefore be used to bend or straighten the second bending portion 25. Herein, a position of the second wire defines one direction in which the second bending portion 25 can be bent.

The present invention is not limited to the aforesaid embodiment, but can be modified in various aspects with the gist of the invention left unchanged.

As described so far, according to the present invention, a second bending portion is made shorter than a first bending portion. This results in an endoscope that can be angled readily while being unaffected by the state of a lumen into which the endoscope is inserted.

According to the present invention, it is apparent that a wide range of different embodiments can be formed based on the invention without a departure from the spirit and scope of the invention. The present invention is limited to the appended claims but not restricted to any specific embodiment.

What is claimed is:

1. An endoscope comprising:
   a first bending portion that is the distal portion of an elongated insertion member, the first bending portion being bendable in accordance with the bending operation by a user; and
   a second bending portion that is located at the proximal end of said first bending portion and whose dimension in the longitudinal direction of said insertion member is smaller than that of the first bending portion, the second bending portion being bendable in accordance with the bending operation by a user;

wherein a bending angle said first bending portion assumes when bent is set and a bending angle said second bending portion assumes when bent is set are determined so that when said second bending portion is bent by an angle θ and said first bending portion is bent by an angle θ+90° or more in a direction opposite to the direction in which said second bending portion is bent, if the distal portion of said insertion member is angled substantially perpendicularly to the longitudinal direction of said insertion member, the distal portion of said insertion member will be distanced from a tangent to the longitudinal direction of said insertion member.

2. The endoscope according to claim 1, wherein:

said first bending portion can be bent in four directions substantially perpendicular to the longitudinal direction of said insertion member; and said second bending portion can be bent in at least two directions perpendicular to the longitudinal direction of said insertion member.

3. The endoscope according to claim 1, wherein a bending angle the first bending portion assumes when bent is set is larger than a bending angle the second bending portion assumes when bent is set.

4. An endoscope according to claim 3, wherein said second bending portion is passively bendable in four directions substantially perpendicular to the longitudinal direction of said insertion member.

5. The endoscope according to claim 3, wherein the directions in which said second bending portion is bendable are agreed with two directions out of the directions in which said first bending portion is bendable, said two directions are opposite to each other.

6. An endoscope comprising:

a first bending portion that is the distal portion of an elongated insertion member;

a second bending portion that is located at the proximal end of said first bending portion and whose dimension in the longitudinal direction of said insertion member is smaller than the dimension of the first bending portion therein;

a first control portion included in a hand-held unit proximal to said insertion member and used to bend said first bending portion; and a second control portion included in the hand-held unit proximal to said insertion member and used to bend said second bending portion;

wherein a bending angle said first bending portion assumes when bent is set and a bending angle said second bending portion assumes when bent is set are determined so that when said second bending portion is bent by an angle θ and said first bending portion is bent by an angle θ+90° or more in a direction opposite to the direction in which said second bending portion is bent, and when the distal portion of said insertion member is angled substantially perpendicularly to the longitudinal direction of said insertion member, the distal portion of said insertion member will be distanced from a tangent to the longitudinal direction of said insertion member.

7. The endoscope according to claim 6, wherein:

said first bending portion is bendable in four directions substantially perpendicular to the longitudinal direction of said insertion member; and said second bending portion is bendable in at least two directions perpendicular to the longitudinal direction of said insertion member.

8. The endoscope according to claim 6, wherein said first control portion is included in the distal part of a control section, and said second control portion is included in the proximal part of the control section.

9. The endoscope according to claim 6, wherein a bending angle said first bending portion assumes when bent is set is larger than a bending angle said second bending portion assumes when bent is set.

10. The endoscope according to claim 6, wherein said second bending portion is passively bendable in four directions substantially perpendicular to the longitudinal direction of said insertion member.

11. The endoscope according to claim 6, wherein the directions in which said second bending portion is bendable are agreed with two directions out of the directions in which said first bending portion is bendable, said two directions are opposite to each other.

12. The endoscope according to claim 6, wherein the axis of rotation of said first control portion and the axis of rotation of said second control portion are extended in different directions.

13. The endoscope according to claim 6, wherein:

said first control portion is located so that when said hand-held unit is held, said first control portion will lie within reach of a finger of the hand with which said hand-held unit is held; and said second control portion is located so that when said hand-held unit is held, said second control portion will lie beyond reach of a finger of the hand with which said hand-held unit is held.

14. The endoscope according to claim 6, wherein an electric switch subsection used to give predetermined instructions is interposed between said first control portion and said second control portion.

15. The endoscope according to claim 6, wherein said first control portion is located in the distal part of a control section, and said second control portion is located in the proximal part of the control section.

16. The endoscope according to claim 6, wherein said first control portion is arranged so that when said hand-held unit is held, said first control portion will lie within reach of a finger of the left hand with which said hand-held unit is held; and said second control portion is arranged so that when said hand-held unit is held, said second control portion will lie beyond reach of a finger of the left hand with which said hand-held unit is held, and will be manipulated with a finger of the right hand.

17. The endoscope according to claim 6, wherein said first control portion includes a first Right/Left control member that is used to bend said first bending portion in a Right or Left direction, and a first Up/Down control member that is used to bend said first bending portion in an Up or Down direction.

18. The endoscope according to claim 6, wherein said second control portion includes a second Up/Down control member that is used to bend said second bending portion in an Up or Down direction.

19. The endoscope according to claim 12, wherein the axis of rotation of said first control portion and the axis of rotation of said second control portion are extended substantially parallel to each other.

20. The endoscope according to claim 12, wherein the axis of rotation of said first control portion and the axis of rotation of said second control portion are extended substantially perpendicularly to each other.

21. The endoscope according to claim 14, wherein said electric switch subsection separates said first control portion and said second control portion from each other.

22. The endoscope according to claim 15, wherein a manipulated portion of said first control portion and a manipulated portion of said second control portion face in the same direction.

23. An endoscope comprising:
a first bending portion that is the distal portion of an elongated insertion member, the first bending portion being bendable in accordance with the bending operation by a user; and
a second bending portion that is located at the proximal end of the first bending portion and whose dimension in the longitudinal direction of the insertion member is larger than that of the first bending portion, the second bending portion being bendable in accordance with the bending operation by a user.

24. An endoscope comprising:
a first bending portion that is the distal portion of an elongated insertion member;
a second bending portion that is located at the proximal end of said first bending portion and whose dimension in the longitudinal direction of said insertion member is larger than the dimension of the first bending portion therein;
a first control portion included in a hand-held unit proximal to said insertion member and used to bend said first bending portion; and
a second control portion included in the hand-held unit proximal to said insertion member and used to bend said second bending portion.

25. The endoscope according to claim 18, wherein the second control portion further includes a second right/left control member that is used to bend the second bending portion in a Right or Left direction.

26. The endoscope according to claim 1, wherein the first bending portion is bendable under the control of a first control portion; and
the second bending portion is bendable under the control of a second control portion.

27. The endoscope according to claim 6, the first control portion and the second control portion are located in different positions.

28. The endoscope according to claim 27, wherein the first control portion is arranged so that when the hand-held unit is held, the first control portion will lie within reach of a finger of the hand with which the hand-held unit is held; and
the second control portion is arranged so that when the hand-held unit is held, the second control portion will lie beyond reach of a finger of the hand with which the hand-held unit is held.

29. The endoscope according to claim 26, wherein the first bending portion can be bent in four directions substantially perpendicular to the longitudinal direction of the insertion member; and
the second bending portion can be bent in at least two directions perpendicular to the longitudinal direction of the insertion member.

30. The endoscope according to claim 26, wherein a bending angle the first bending portion assumes when bent is set is larger than a bending angle the second bending portion assumes when bent is set.

31. The endoscope according to claim 26, wherein the second bending portion is passively bent in four directions substantially perpendicular to the longitudinal direction of the insertion member.

32. The endoscope according to claim 26, wherein the direction in which the second bending portion is bent are arranged with two directions in which the first bending portion is bent, the two directions are opposite to each other.

33. The endoscope according to claim 1, wherein said second bending portion accommodates a larger number of built-in components than said first bending portion.

34. The endoscope according to claim 6, wherein said second bending portion accommodates a larger number of built-in components than said first bending portion.

35. The endoscope according to claim 23, wherein said second bending portion accommodates a larger number of built-in components than said first bending portion.

36. The endoscope according to claim 24, wherein said second bending portion accommodates a larger number of built-in components than said first bending portion.

37. An endoscope comprising:
a first bending portion that is the distal portion of an elongated insertion member, the first bending portion being bendable in accordance with the bending operation by a user; and
a second bending portion that is located at the proximal end of said bending portion, the second bending portion being bendable in accordance with the bending operation by the user,
wherein said second bending portion has its length different from that of said first bending portion and a bending angle said first bending portion assumes when bent is set and a bending angle said second bending portion assumes when bent is set are determined so that when said second bending portion is bent by an angle θ and said first bending portion is bent by an angle θ90° or more in a direction opposite to the direction in which said second bending portion is bent, if the distal portion of said insertion member is angled substantially perpendicularly to the longitudinal direction of said insertion member, the distal portion of said insertion member will be distanced from a tangent to the longitudinal direction of said insertion member.

38. The endoscope according to claim 37, wherein said second bending portion accommodates a larger number of built-in components than said first bending portion.

* * * * *